(12) United States Patent
Flanagan et al.

(10) Patent No.: US 6,635,282 B1
(45) Date of Patent: Oct. 21, 2003

(54) GELLAN GUM TABLET FILM COATING

(75) Inventors: John Flanagan, Neshanic Station, NJ (US); George Colegrove, San Diego, CA (US); Thierry Nivaggioli, San Francisco, CA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/570,025

(22) Filed: May 12, 2000

Related U.S. Application Data (63) Continuation-in-part of application No. 09/308,043, filed as application No. PCT/US98/23430 on Oct. 30, 1998, now Pat. No. 6,395,298.
(60) Provisional application No. 60/064,454, filed on Oct. 31, 1997.

(51) Int. Cl.[7] .............................. A61K 9/34; A61K 47/36
(52) U.S. Cl. ........................................ 424/479; 424/481
(58) Field of Search ................................ 424/429, 481; 427/2.23; 514/777

(56) References Cited

U.S. PATENT DOCUMENTS

| | | |
|---|---|---|
| 4,326,052 A | 4/1982 | Kang et al. |
| 4,385,123 A | 5/1983 | Kang et al. |
| 5,334,640 A | 8/1994 | Desai et al. |

FOREIGN PATENT DOCUMENTS

| | | |
|---|---|---|
| EP | 048123 | 3/1982 |
| EP | 00481231 | 3/1982 |
| EP | 0 630 580 | 12/1994 |
| JP | 62-125850 | 6/1987 |
| JP | 62-132831 | 6/1987 |
| JP | 09-020649 | 1/1997 |
| WO | WO 94/18954 | 9/1994 |
| WO | WO 95/28927 | 11/1995 |
| WO | WO 96/36321 | 11/1996 |

OTHER PUBLICATIONS

"Simple Films and coatings made with Gellan Gum" Research Disclosure, Kelco Division of Merck and Co., Inc., May 1994.

"Gellan Gum Coating and Adhesion Systems" Research Disclosure, Kelco Division of Merck and Co., Inc. Jun. 1993.

Primary Examiner—Edward J. Webman
(74) Attorney, Agent, or Firm—Banner & Witcoff, Ltd.

(57) ABSTRACT

A film coated tablet wherein the tablet is film coated with a gellan gum coating composition containing gellan gum, a plasticizer, and a disintegration aid. Optionally a slip enhancer is added to the composition. A method for coating a tablet with the gellan gum composition wherein the composition is applied as a solution. A method of administering the gellan gum film coated tablet as a pharmaceutical.

21 Claims, 1 Drawing Sheet

FIG. 1

GELLAN GUM TABLET FILM COATING

This application is a continuation-in-part of U.S. application Ser. No. 09/308,043, filed Sep. 24, 1999, now U.S. Pat. No. 6,395,298, which is a 371 of PCT/US98/23430, filed Oct. 30, 1998, which is a continuation-in-part of Provisional Application No. 60/064,454 filed Oct. 31, 1997, each of which is incorporated by reference in its entirety.

FIELD OF THE INVENTION

This invention relates generally to tablet coatings and to a method to prepare compositions useful to coat tablets. More particularly this invention relates to a gellan gum coated tablet, a tablet coated with a gellan gum composition, a gellan gum composition useful to coat a tablet, a method for coating a tablet with gellan gum, and a method of using a gellan gum coated tablet.

BACKGROUND OF THE INVENTION

Tablets are typically used to deliver a pharmacologically effective amount of a therapeutic drug to humans and animals so as to provide medicinal benefit to the human or animal. Typically such therapeutically effective drugs include those drugs that possess and produce desirable drug effects after effective consumption by the human or animal.

In medicinal uses, one or more coatings is desired on a medicinal tablet in order to obtain one or more of gloss, better appearance, identification, mouthfeel, stability, color, swallowability, improved taste and the like.

Many medicinal tablet coatings today are low viscosity hydroxypropylmethyl-cellulose (HPMC). Usually a HPMC solution of about 10% weight with a viscosity below 1000 cps. (centipoise), with or without an appropriate plasticizer, is applied by a spraying system or device to a tablet in a coating process.

Even with the foregoing and other tablet coating compositions, the industry continues to desire a product which provides enhanced tablet coating properties. The industry has recognized the need for an improved tablet coating which would provide increased gloss, better mouthfeel at coating quantities at lower levels than conventionally accepted methods, for example. The process of preparing such an improved tablet coating economically and efficiently continues to be of interest.

In addition to the aesthetics and economics, tablet coatings are required to release the drug in the tablet. To do this, tablets coatings must have minimal or no detrimental effect on dissolution and disintegration tests that are performed on tablets.

OBJECTS OF THE INVENTION

It is an objective of the invention to provide a gellan gum film coated tablet.

It is another objective of this invention to provide a film coated tablet having a coating composition comprising gellan gum.

It is an additional objective of this invention to provide a gellan gum composition useful for coating tablets.

It is yet another objective of this invention to provide a process for preparing a film coated tablet.

It is another objective of this invention to provide a gellan gum coated placebo or a film coated pharmaceutical tablet comprising an active drug.

It is yet still an additional objective of this invention to provide a tablet having one or more enhanced properties such as higher gloss, better mouthfeel, non-tackiness, better taste, being swallowable with little or no accompanying liquid and easier to swallow than commercially available forms, and the like.

The above objectives and other objectives are met in this invention which is more particularly described hereinafter without limitation.

SUMMARY OF THE INVENTION

In one embodiment, this invention comprises a film coated tablet, the coating comprising gellan gum, a plasticizer, and a disintegration aid. Optionally, the coating further comprises a slip enhancer. In another embodiment, the tablet comprises a placebo or an active drug or pharmaceutical wherein the placebo or drug is film coated with the gellan gum film coating. In another embodiment this invention further comprises coating a tablet with an aqueous gellan gum composition comprising the steps of admixing gellan gum, a plasticizer, a disintegration aid, optionally a slip enhancer, and water under effective shear conditions to prepare an aqueous gellan gum coating composition and applying the same in an adherent fashion to a tablet whereby a gellan gum film coated tablet and optionally thereafter drying the same. In yet another embodiment of this invention, this invention comprises a method of treating a patient in need of treatment which comprises administering to the patient a therapeutically effective amount of a film coated tablet, the coated tablet having a film coating comprising gellan gum, a plasticizer, a disintegration aid and optionally a slip enhancer; the tablet containing a therapeutically effective amount of a drug beneficial to said patient. Other embodiments of this invention are included herein and are described in more detail hereinafter.

DETAILED DESCRIPTION OF THE INVENTION

The present invention is directed to a gellan gum coated tablet. In order to form the coating on the tablet, an aqueous composition is prepared containing at least gellan gum, and effective amounts of a plasticizer and a disintegration aid. Optionally, the composition further comprises a slip enhancer. The ingredients may be combined in any suitable order, and two or more ingredients may be premixed prior to combining with the remaining ingredients.

Gellan gum useful herein is that produced by inoculating a carefully formulated fermentation medium with the microorganism Sphingamonas elodea (ATTC 31461). Gellan Gum is available from Monsanto Company, 800 North Lindbergh Boulevard, St. Louis, Mo. 63167, USA. Typical brand names include KELCOGEL and GELRITE. Gellan gum useful herein includes any form available form such as but not limited to, non-clarified, clarified, and partially-clarified native, deacetylated and partially deacetylated forms as well as mixtures thereof and the like. KELCOGEL and GELRITE are registered trademarks of Monsanto Company. Gellan gum may be prepared according to the methods disclosed in U.S. Pat. Nos. 4,326,052 and 4,385,123 both of which are incorporated herein their entirety by reference.

The amount of gellan gum in the aqueous gellan gum composition is about 0.1% to about 10% and preferably from about 0.5% to about 5% by weight gellan gum of the total gellan gum aqueous composition although greater and lesser amounts of gellan gum may be employed if desired. A most preferred range is about 0.5% to about 3.5%.

The aqueous gellan gum composition also contains plasticizer. The plasticizer increases the elasticity of the coating to provide a smooth coating that will not crack. The plasticizer provides an improved appearance by eliminating or minimizing cracking, peeling, nicking, picking, and off color. Preferred plasticizers include propylene glycol, polyethylene glycol 400, polyethylene glycol 3350, polyethylene glycol 8000, glycerol triacetate, polysorbate 80, triethyl citrate, PLAS 2 (glycerol monostearate, Polysorbate 80, triethyl citrate), acetylated monoglycerides (MYVACET 9-45). Other suitable plasticizers include, but are not limited to, glycerine, dibutyl sebacate, acetyltributyl citrate, and acetyltriethyl citrate. Any equivalent or substantially equivalent plasticizer may be satisfactorily employed herein. The term plasticizer also includes the use of more than one plasticizer.

The plasticizer is added in an amount effective to provide the desired elasticity. Generally, about 0.01 wt % to about 10 wt % plasticizer based on the total gellan gum aqueous composition is used, preferably about 0.01 wt % to about 5 wt %, and most preferably about 0.05% to about 2.5 wt %.

Because the plasticizer provides elasticity to the coating which avoids cracking of the tablet coating, it also increases the disintegration and dissolution times of the coated tablet. Thus, a disintegration or dissolution aid is added to the aqueous gellan gum composition to aid in the disintegration of the coating on the film coated tablet allowing increased drug dissolution and availability. Suitable disintegration aids include, but are not limited to lecithin, pregelatinized modified corn starch, glyceryl carpylate, sorbitan oleate, and sodium lauryl sulfate. The term disintegration aid also includes the use of more than one disintegration aid.

The disintegration aid is added in an amount to achieve the desired drug disintegration or dissolution rate, improve adhesion, improve slip, improve mouthfeel, and/or reduce tack of films and finished dosages. The amount depends on the chemistry of the tablet composition, the tablet shape and physical characteristics of other coatings present, and how quickly the drug should be made available to the recipient. As the amount of the disintegration aid increases, the disintegration time decreases allowing faster drug availability. Generally, up to about 10 wt % disintegration aid based on the total gellan gum aqueous composition is used, preferably up to about 5 wt %, and most preferably about 0.05% to about 2.5 wt %.

The aqueous gellan gum composition may also contain a sequestrant such as, but not limited to, sodium citrate, ammonium citrate, potassium citrate, EDTA, and mixtures thereof. The amount of sequestrant is an amount sufficient to provide the ions necessary to allow hydration and gelling of the gellan gum within acceptable processing temperature ranges, generally 0 to about 5 wt %, preferably 0 to about 1 wt % and most preferably about 0.05 to about 0.6 wt % sequestrant based on total weight of the aqueous composition.

Prior art gellan gum coating systems utilizing only gellan gum provide coatings having a low permeability to water and high disintgration and dissolution times. Utilizing the system of the invention, water permeability increases resulting in a decrease in disintegration and dissolution times. Not only is water permeability increased, the aesthetics of the film coating have been retained and improved.

The aqueous gellan gum composition may also contain preservatives such as, but not limited to, methyl paraben, propyl paraben, benzoic acid, EDTA or mixtures thereof. The amount of preservative is generally 0 to about 1 wt % based on the total weight of the aqueous gellan gum composition, preferably 0 to about 0.5 wt %, and most preferably 0 to about 0.3 wt %.

The aqueous gellan gum composition may also contain one or more of another ingredient including a polymer such as, but not limited to, hydroxypropyl cellulose, hydroxypropyl methyl cellulose, sodium carboxymethyl cellulose, alginic acid, sodium alginate, gum acacia, gelatin, CMC, sodium CMC, polydextrose, povidone, sugar, aspartame, maltodextrin, tapioca dextrin, modified food starches, polyvinyl-pyrolidone, mixtures thereof, and the like may be employed in this invention. As employed herein, the term "gellan gum" includes gellan gum and/or compositions of gellan gum with one or more of these polymers or a sugar.

The aqueous gellan gum composition may contain a suitable color or colorants or color systems for application to a colored or noncolored coated or uncoated tablet. Illustrative colors and colorants useful herein include without limitation, pigments, dyes, lakes, and oxides (including titanium dioxide) and the like, may be optionally employed with gellan gum used in practicing this invention.

In addition, various other ingredients may be employed in the gellan gum aqueous composition including any ingredient which is compatible or can be made compatible with an aqueous gellan gum composition useful to coat tablets of this invention. Such other ingredients include, but not limited to, flavor(s), sweetener(s), mint(s), fragrance(s), active ingredient(s) and mixtures thereof and the like.

Suitable sweeteners include, but are not limited to, corn syrup solids, sucrose, aspartame, neotame, maltilol, maltilol syrup, neosorb, xylitol, acesulfame, Sweet Am, fructose, brown sugar, Stevia (Butterfly Brand & Wisdom of the Ancients.) Flavors include, but are not limited to, cherry, mint, spearmint, peppermint, wintergreen, banana, coconut, wild cherry, grape, tooti fruiti, cinnamon, strawberry, orange, root beer, bubble gum, and chocolate.

The process for preparing a film coated tablet comprises the steps of admixing gellan gum, plasticizer, disintegration and processing aids, and water under effective shear, heat, and ionic conditions to prepare an aqueous gellan gum coating composition and applying the aqueous gellan gum coating composition in an effective fashion to the tablet whereby a gellan film coated placebo or film coated pharmaceutical tablet is formed a drying step typically occurs and typically follows.

The aqueous gellan gum film coating composition is preferably admixed in any suitable container or the like prior to applying the aqueous gellan gum composition to or on a tablet to be coated. Initially the gellan gum and water are admixed and further mixing is carried out under effective shear to form an aqueous film tablet coating composition.

The aqueous gellan gum composition of this invention may be mixed in or by any suitable mixing system preferably until substantially complete mixing has been accomplished. Some heating may be necessary to achieve dispersion and hydration of gellan gum. The amount of shear preferably employed is an effective amount, i.e., which produces a well mixed homogenous gellan gum composition. The aforementioned admixing can be carried out by any convenient means including but not limited to use of a propeller or stirrer system although generally stirring by a convenient mechanical means is acceptable. Other forms of mixing can be employed.

Typically the gellan gum coating aqueous composition prior to application of effective shear will have a viscosity in the range from about 44 cps. to about 55,500 cps. and preferably from about 2200 to about 50,000 cps although gellan gum compositions having greater and lesser viscosities may be employed depending on a number of factors. Historically those of skill in the art have considered a composition having a viscosity of about 1,000 centipoise (cps) as being at the upper bound as regards usefulness as a coating composition due to that high viscosity. Since an aqueous composition comprising gellan gum (1.8% by weight gellan gum) and water has a viscosity of about 28,460 cps at a temperature of about 30° C., those of skill in the art would not have considered such a composition useful to coat tablets and would have been steered away from it for this invention. Now, however, the inventors have surprisingly discovered that despite the high viscosity of a gellan gum composition at room temperature that such compositions are very useful to film coat tablets as the invention herein provides.

The gellan gum aqueous composition is preferably applied to the tablet(s) to be coated in a batch, semi-continuous, or continuous process or some combination thereof in a manner which produces a satisfactorily uniformly coated tablet. The gellan gum composition may be applied to tablets to be coated using any satisfactory application and drying system or combination of some application system and some drying system.

During application of the gellan gum aqueous composition to the tablet to be film coated, the temperature of the gellan gum aqueous composition is preferably in the range from about 25° C. to about 55° C. although greater or lesser temperatures may be employed if desired. It is preferred that the gellan gum composition be maintained in a solution or dispersion or an applicable state during its coating application to the tablet(s) to carry out this invention.

In the text "Pharmaceutical Dosage Forms: Volume 3 (second edition by Lieberman, Lachman, and Schwartz) and in Pharmaceutical Coating Technology (Cole, Hogan, and Aulton) the process of film coating is described in detail. The steps of film coating include: spraying (atomizing the coating solution), droplet formation (individual drops of coating material in solution), impingement, wetting, spreading, and then coalescence, adhesion, and cohesion. Evaporation and cooling begin during droplet formation. In the present invention, the coating is applied onto the tablet as an aqueous solution which subsequently gels and forms a film after being applied to the tablet while still in solution. That is, the droplets impinge on the tablets with the gellan gum still in solution thus allowing wetting, spreading, and coalescence to occur. The resulting film is uniform, thin, and very shiny (has a high gloss).

Gellan gum preparations gel at specific temperatures based upon the concentration and type of ions present. In prior art processes, the gel actually forms during the spraying step resulting in the gel, not the aqueous solution, being applied to the tablet. For example, when the droplet leaves the spray gun, it is traveling at about 50 miles per hour. The droplet size and traveling speed, coupled with the cooling effect of evaporation and spray shear, lowers the droplets temperature below the gel temperature and causes gel formation. The gelled material then adheres to the surface of the tablet forming a sticky, rough surface, not a uniform film. It is impossible to obtain a smooth surface having high gloss when the gel is formed prior to deposition on the tablet.

In order to obtain the desired film, two unique processing parameters are used that differ from standard coating procedures. The first parameter is the air pressure used for atomization. Industry typically requires a nozzle pressure of about 45 to 60 psi, whereas the invention uses about 22 to about 29 psi, preferably about 25 psi. The second parameter is the distance from the nozzle to the product bed. Industry typically requires distances of 8 to 12 inches (depending upon the particular equipment used,) whereas the invention uses distances of about 2 to about 4 inches. These processing parameters allow the gellan to be deposited onto the tablet surface while still in solution and then form a uniform, elegant film.

The aqueous gellan gum composition may be coated onto tablets which are uncoated or have been coated with one or more prior coatings (overcoating) of an acceptable coating composition which allows adherency with gellan gum. For example, an initial coating may comprise one or more polymers such as cellulosics, dextrins, acrylics, colors, or other pharmaceutical coating material.

The aqueous gellan gum composition may be applied as at least one of a primary coating, a secondary coating, or a tertiary coating as desired. One or more coating applications of gellan gum may be made to a coated or uncoated tablet in accordance with this invention, although typically one coating is effective and is preferred. If desired, a gellan gum coating may be applied to a tablet in accordance with the invention in an instance wherein a protective coating is desired, for example to protect coated or uncoated tablet from physical damage.

The gellan gum composition is coated onto the tablets in an amount sufficient to achieve the desired appearance, feel, and disintegration rate. As the total coating solids weight gain increases, the disintegration time increases. For example, as the weight gain of the tablet increases from 0 to 0.5% due to application of a gellan gum coating, the disintegration time can increase from 0 to 50 minutes.

The amount of coating provided to the surface of the tablet is an effective amount and is typically that amount which provides a minimum effective coverage of the exterior surface area of the tablet, although this invention also encompasses those instances where there is partial coverage of the exterior surface as well.

Typically the amount of gellan gum which is film coated onto tablets in practicing this invention is that amount which provides a gellan gum film coated tablet having a weight gain (during coating) from about 0.025% to about 10% weight percent of the total tablet weight and preferably from about 0.05% to about 5% weight percent of the total tablet weight although larger and smaller weight percents may be employed if desired. Typically this amount of gellan gum is that amount which is necessary to provide an effective or desired coating.

The tablet may be a placebo (blank) or may contain an active ingredient. Active ingredients which may be effectively coated using this invention are not limited and include illustratively pharmaceutical active ingredients and over-the-counter drugs (including vitamins and nutritional supplements and the like) such as those typically delivered in a tablet dosage form. Examples include but are not limited to analgesics and antiphlogistics such as aspirin, acetaminophen, phenacetin; steroids including antiinflammatory steroids; enzymes, proteins, antibiotics or antimycrophotics including penicillin and its derivatives; anesthetics, vasodiolators such as nitroglycerin, anticarcinogins, sulfonamide drugs, sedatives, tranquilizing and hypnotic agents, bronchial-dilating agents, potassium chloride, mixtures thereof and the like. It is emphasized that the invention is not limited to any particular active ingredient or therapeutic category.

Preferred tablets are medicinal tablets for humans or animals. The tablets include but are not limited to tablets of any convenient composition which may or may not contain any pharmaceutically effective drug, vitamin or nutrient or drugs suitable for human and/or animal consumption.

Tablets to be coated according to this invention may be colored, neutral or have their natural color or may be absent of color. If one of more colors, dyes lakes, or pigments or mixtures thereof are employed in a gellan gum coating composition herein, such as for example, an FDA certified color, dye, lake, or pigment, the color or combination of colors is not critical and may be selected by those of skill in the art based upon a need at the time of the coating operation. Examples of suitable pigments which are useful in this invention include, without limitation, FD&C and D&C lakes, titanium dioxide, magnesium carbonate, talc, pyrogenic silica, iron oxides, channel black, insoluble dyes and mixtures thereof and the like. Also, nature pigments such as riboflavin, carmine 40, curcumin, annatto, mixtures thereof and the like are acceptable herein. Other examples of pigments suitable herein include, without limitation, these disclosed in Jeffries U.S. Pat. No. 3,149,040 and Butler et al., U.S. Pat. No. 3,297,535, as well as in Colorcon U.S. Pat. No. 3,981,984. These three patents are incorporated herein by reference in their entirety. In the absence of a colorant, the gellan gum composition typically produces a clear or substantially clear coating on a coated tablet.

Neither the tablet shape nor the tablet size are critical. Preferred shapes and sizes are those which can be effectively consumed by a human or animal recipient with relative ease. Preferable sizes of tablets include but is not limited to those tablets which are about ¼ inch to about ¾ inch in size and weigh from about 100 milligrams to about 1.9 grams each although tablets may be employed which are larger or smaller in size and of lighter and heavier weight if desired. Preferred shapes are round or oval; however, other shapes may be employed if desired.

Tablets useful herein include but are not limited to tablets which are uncoated or have been coated one or more times. In one embodiment a gellan gum coating may be the only coating and may comprise a first coating or a second or a third coating.

As employed herein, the term "tablet" includes without limitation, tablet, particle, micronized particle, particulate, pellet, pill, core, powder, granule, granulate, small mass, seed, specks, spheres, crystals, beads, agglomerates, mixtures thereof and the like. Typically the preferred tablet will be in a form sufficiently stable physically and chemically to be effectively coated in a system which involves some movement of the tablet. Virtually any tablet, placebo, the latter typically lactose or sugar or mixtures thereof and the like, is acceptable herein as a tablet to be coated in the practice of this invention.

Tablets coated according to this invention have a high gloss. Typically the gloss is in the range from about 200 to about 400 and preferably from about 250 to about 350 although greater or lesser gloss may be employed if desired. As referred to above, gloss is measured or characterized typically by use of a Tricor Systems, Inc., Model 805A, Surface Analysis System. Tablets of this invention typically have one or more enhanced properties such as higher gloss, better mouthfeel, non-tackiness, being swallowable with little or no accompanying liquid, better taste and the like.

The gloss resulting from gellan gum film coating of this invention is superior in shine to conventional film coatings presently used in the industry and previously disclosed gellan coatings. Measurements of gloss on polymer coated tablets and commercial products were well below the gloss imparted with gellan gum prepared in accordance with this invention as measured by a "Surface Analysis System" (Model 805A) which is manufactured by TRICOR Systems Inc. Gellan gum coatings of this invention impart this gloss at weight gain levels that are considerably lower than existing and accepted alternatives. As a result of this high gloss from comparatively lower weight gains brought about by this invention, gellan gum is an attractive alternative to existing aqueous film coatings.

Generally, the greater the amount of weight gain of the tablet due to gellan gum film coating, the higher the gloss of the coating until a maximum gloss is obtained at a tablet weight gain of about 0.2 to about 0.6 wt %.

This characteristic high gloss from low weight gains also makes gellan gum an attractive alternative to sugar coating processing currently used in the industry. Sugar coating processes currently use multiple materials, extended processing times and multiple material handling steps. Superior gloss can be achieved with gellan gum at a fraction of the weight gain now required in sugar coating. This lower material requirements results in glossy tablets that can be manufactured much faster than current products and can also be formulated to produce a smaller, easier to swallow dosage.

As employed herein, the term "adherent" means that the gellan gum coating effectively adheres to the coated tablet until consumption by a patient or animal to enable effective release of the active ingredient therefrom so that the active is effectively made available to the patient's biological systems to provide therapeutic value.

Although the gellan gum coating composition of this invention will initially be an aqueous composition, the tablet coating will preferably be dried or substantially dried prior to, upon its exit or removal from the coating application system or at sometime in preparing coated tablets. The coated tablets may be placed in suitable packaging then if desired.

If desired, one or more layers of gellan gum film coating may be employed using this invention. Those of skill in the art will be able to determine the extent of any layering depending on the drug, tablet size, and its physical and chemical and therapeutic properties and characteristics from a reading of this specification and using their skill in the art.

It is preferred that the film coating be continuous or nearly continuous and over the surface of the tablet. An effective depth of the film coating is provided for retention. It is also desired that the tablet film coatings herein be somewhat resilient with respect to handling, to peeling and to flaking and being rubbed off the coated tablet.

As referred to above, application of the gellan gum aqueous composition as a film coating to the tablet is preferably carried out by placing a tablet capable of receiving and adhering a gellan gum tablet coating composition of this invention in any acceptable coating application system. An acceptable coating application system is illustratively any system which has the capability to apply a gellan gum coating composition of this invention to a tablet to provide an effectively, preferably uniformly coated tablet. For example, an acceptable coating application system includes without limitation, a plain fluid bed system (i.e., one without any "Wurster" type insert), including a fluid bed spray tower of any reasonable size and design and systems similar thereto in function and utility.

Air Suspension Coating systems useful here as an illustrative application system include those described in Ullman's Encyclopedia of Industrial Chemicals, Volume A 16 pages 583–584 (1990) which includes a description of the Wurster process. Ullman's Encyclopedia of Industrial Chemicals, Volume A16 pages 583–584 (1990–1996) is incorporated herein by reference in its entirety. This incorporation includes the chapter Microencapsulation authored by Christopher a. Finch of Pentafin Associates, Weston Turville, AYLESBURY HP 22 5TT, UK.

Also, acceptable for use to prepare coated tablets of this invention are illustratively a variety of side vented coating pans, spray dryer(s), continuous coating pans, and conventional coating pans, such as those with systems for mechanically providing the gellan gum composition to a tablet in an effective manner using mechanical means as for example by spray nozzles or the like. Also acceptable as a spray tower system is a conventional fluid bed tower equipped with a suitable spray apparatus. Any application system capable of applying a composition of this invention to a tablet is an acceptable system for coating tablets employing the aqueous gellan gum coating composition of this invention. As the coating system is not critical, any size coating system is acceptable. Batch and continuous processes, semi-continuous and suitable variations thereof are envisioned without limitation.

The "Wurster" type fluid bed dryer typically comprises a cylindrical outer vessel having a perforated floor through which a heated gas passes upwardly to heat and fluidized a batch of tablets or particles fed to or formal therein a concentric, open ended inner cylinder is suspended above the center of the perforated floor of the outer vessel a spray nozzle, or projecting part, centered beneath the inner cylinder sprays a solution of the coating material upwardly into the inner cylinder as the fluidized materials pass upwardly through the spray in the inner cylinder. The particles circulate upwardly though the center of the inner cylinder and downwardly between the inner and outer cylinder. The air that fluidizes the particles also serves to vaporize the water causing the composition to deposit as a film or coating onto the surface of each particle. After repeated passes through the coating zone in the inner cylinder, a sufficient thickness of polymer accumulates over the entire surface of each particle as to coat each particle. A description of an acceptable "Wurster" type fluid bed dryer is found in J. Am Phar. Assoc, Sci. Ed. Vol 48, (1959) Air Suspension Technique of Coating Drug Particles by Wurster, Dale E. and Preparation of Compressed Tablet Granulations by the Air Suspension Technique II, Wurster, Dale E, Sci Ed Vol 49 (1960) both of which are incorporated herein in their entirety by reference. In operation of the dryer, the operator will typically have the tablets discharged when the desired amount of coating has been applied to the tablets. This is generally based on the amount of coating composition sprayed in the dryer from which based on prior experience, the amount of weight gain (%) of the tablets during coating can be determined. Electronic or equivalent controls are typically installed on the dryer to regulate the process such as regulating the temperature of the inlet air and the amount of such inlet air and its pressure.

In side vented coating pan systems, as the material inside is coated it increases in size and weight. Generally the materials to be coated accumulate adjacent an end wall and along a side wall of the drum in the system. As the drum rotates, the material is tumbled and is coated with a coating composition from one or more spray nozzles. Initially the material may form a mass and as the material is sprayed and increased in size the large particles migrate away from the end wall and cannot penetrate the mass of smaller particle adjacent the end wall. Eventually, substantially all of the material is uniformly coated a such that the material forms a new mass wherein the particles are slightly larger than the original mass formed by the uncoated particles. The process repeats itself such that the particles are coated with additional composition from the spray nozzle, thereby again increasing in size and weight and migrating away form the end wall. The cycle continues until the particle achieve a desired uniform size.

Particularly useful self contained side vented coating pan system in this invention are available under the Accela Cota brand sold by Thomas Engineering Incorporated, 575 West Central Road, Hoffman Estates, Ill., 60195-0198, U.S.A. Various size pans may be satisfactorily employed herein and include without limitation 15, 24, 48 and 60 inch pans, if desired. The size of the pan and dryer are not critical. The Compu Lab model sold under the Accela Cota brand works well for laboratory size charge (feed) quantities. Those of skill in the art will recognize that various size pans may be employed depending on the amount of materials to be coated and other coating operations.

The Accela Cota brand side vented coating pan system comprises a rotating drum and as the drum is rotated containing the tablets to be coated, the coating composition is applied to the tablets by means of one or more nozzles positioned within the rotating drum so as to direct the coating composition to the tablets in the bed. As the pan is rotated and the coating composition is further applied to the tablets, the tablets achieve a desired coating. This apparatus is also a dryer for substantially drying the tablets as the tablets are coated. The side wall of the drum is perforated and a flow of air is provided into the drum through apertures for drying the coating composition on the tablets a system is also provided on the apparatus for removing the outlet air and for removing the coated tablets.

The nozzles of this side vented coating system are preferably adjustable and may be positioned nearer to and closer to the bed of tablets to be coated depending on the conditions of use and the desired coating composition quality and quantity, among other factors. Those of skill in the art will recognize that the distance of the nozzle or nozzles from the bed is important and may be adjusted to provide optimum coating compositions. In operation such nozzle placement distances will be an effective distance and will be selected from a plurality of available positions and will depend on the tablets being coated, the coating compositions, the degree of coating desired and other conditions of the particular coating operation, among other factors.

Those of skill in the art will recognize that one or more nozzles may be employed as desired to provide optimum coating. The number of nozzles is not critical and may be varied as needed depending on the coating operation and other factors. The nozzle throat diameter is typically from about 0.028 inch to about 0.100 inch although, greater and smaller throat diameters may be employed a nozzle throat diameter of somewhere about 0.040 inch is preferred. The nozzle(s) is preferably aimed perpendicularly or nearly perpendicular to the bed although other direction(s) of aim may be employed if desired. Those of skill in the art will recognize that the pan may be rotated at a speed selected from a plurality of operating speeds. The pan may be stopped after the material has been coated and the matter removed.

In general, an effective nozzle distance for applying a coating to a tablet using a side vented pan coating system is in the range from being positioned less than about a ¼ inch from the bed to about 15 inches and preferably from about 2 to about 4 inches although greater or lesser nozzle distances may be employed if desired depending on the weight of tablets charged into the pan and coating system composition and other factors.

If desired, the same or a similar coating application system can be employed for both a first and a second or sequential coating applications or different coating application systems may be employed for a first or second or more coating applications. If desired, the same coating application system can be used to apply a first and second or more coatings with or without removal of the tablets from such a system between the first and second or more coatings.

While illustrative useful application systems have been described herein, those of skill in the art will recognize that such description is provided to provide information as to the possible application and use herein in accordance with this invention. Those of skill in the art will recognize that the actual operation of any such application system will vary and may be varied from "text book" type description of such operation in according with the parameters and conditions of any desired operation, among other factors. Configurational and design changes may be made on such applications systems and operating parameters may be varied.

The gellan gum coated tablets of this invention may be internally consumed by humans and animals in a typical customary manner.

EXAMPLES

Examples 1–18, are provided to illustrate the preparation of acceptable coated tablets in accordance with this invention and are provided by way of illustration and are not intended to limit the invention in any way. All percents and any parts are by weight unless otherwise indicated. These Examples illustrates the practice of this invention in a non limiting fashion. Various application systems including fluidized feed systems and pan vented coated systems are illustrated without limitation.

EXAMPLE 1

An acceptable high gloss gellan gum film coated (red colored) tablet was prepared in accordance with the following procedure.

A gellan gum composition useful for coating tablets was prepared comprising 30 grams gellan gum, 1968 grams water and two grams sodium citrate to provide a 1.5% by weight gellan gum aqueous composition useful for coating tablets.

This aqueous gellan gum composition was prepared by weighing the water into a clean dry residue free beaker and weighing out the gellan gum (Kelcogel) and sodium citrate. The water was then mixed with a laboratory mixer to create a vortex. The gellan gum powder and sodium citrate was slowly introduced into the vortex to achieve dispersion. Stirring was continued without heat to finalize the dispersion of gellan gum. Heat was applied while stirring until the dispersion temperature was about 70° C. to hydrate the gellan gum. Care was taken to avoid charring the resulting dispersion, i.e. employing sufficient stirring and avoiding overheating. The beaker was removed from the stir plate and cooled to ambient temperature to make the gellan gum aqueous composition available for coating.

The tablets to be coated herein were uncoated placebos (½ inch, standard concave shape, 390 mg. weight each).

A hydroxypropylmethylcellulose (HPMC) and color composition having the ingredients shown in Table 1 below was applied to these uncoated placebos to prepare a tablet which had color and appearance mimicking recognized commercial products using a Compu Lab side vented 15 inch coating pan system as an application system.

TABLE 1

| Ingredients: | Weight (g) |
|---|---|
| Pharmacoat 606 (10%) | 1800 |
| D-447 | 90 |
| TA | 30 |
| Water | 130 |
| Total Weight | 2050 grams |
| Red (D447) (Dye Dispersion) | |
| 11.83% Titanium Dioxide | 23.64 grams |
| 20.01% FD&C Red No. 40, Hi Dye Lake | 40 grams |
| 8.18% FD&C Yellow No. 6 dye | 16.36 grams |
| 2.0% EDTA solution (40%) | 4 grams |
| 57.98% Distilled Water | 115.91 grams |
| | 199.91 grams |

Pharmacoat 606 (10%) = hydroxypropyl methyl cellulose
TA = triacetin (plasticizer)

The side vented pan coating system used herein employed one nozzle which was aimed more or less directly at the bed of tablets to be coated and was positioned at a acceptable standard distance from the outer portion of that bed. That nozzle had a throat diameter of about 0.040 inch. Operating data was:

TABLE 2

Side Vented Coating Pan Operating Data, 1.9 Kg. Charged

| Elapsed Time | Coating Composition Wt (g) | Temperature, ° F. | | PAN | Pan Air Flow | Atomizing Air |
|---|---|---|---|---|---|---|
| (Min) | Sprayed | Inlet | Outlet | RPM | (CFM) | (PSI) |
| 0 | 0 | 72.0 | 49.0 | 10.2 | 238 | 45.2 |
| 4:10 | 38 | 69.5 | 48.5 | 10.2 | 238 | 44.6 |
| 10 | 117 | 68.5 | 49.4 | 10.2 | 238 | 44.3 |
| 15 | 190 | 64.2 | 48.8 | 10.3 | 238 | 44.4 |
| 20 | 261 | 65.1 | 49.0 | 10.3 | 238 | 44.1 |
| 25 | 233 | 60.8 | 47.7 | 10.3 | 238 | 44.2 |
| 30 | 406 | 62.1 | 47.8 | 10.3 | 238 | 44.0 |
| 34:05 | 466 | 61.9 | 47.8 | 10.3 | 238 | 44.1 |

These placebos (red colored) were then coated with the gellan gum aqueous composition (prepared in a first step of this Example) in the same 15 inch diameter pan Compu Lab side vented coating system as an application system, the data of which is shown the following Table 3.

TABLE 3

Side Vented Coating Pan Operating Data Charge = 1.9 Kg. plus color coating

| Elapsed Time | Solution Wt (g) | Temperature, ° F. | | PAN | Pan Air Flow | Atomizing Air |
|---|---|---|---|---|---|---|
| (Min) | Sprayed | Inlet | Outlet | RPM | (CFM) | (PSI) |
| 0 | 0 | 64.5 | 46.6 | 24.3 | 200 | 25.9 |
| 4 | 73 | 61.2 | 41.5 | 24.3 | 220 | 25.4 |
| 8 | 126 | 66.3 | 42.7 | 24.3 | 220 | 25.5 |
| 12 | 178 | 64.8 | 44.5 | 24.3 | 220 | 25.3 |
| 16 | 225 | 65.1 | 47.8 | 24.3 | 220 | 25.2 |

TABLE 3-continued

Side Vented Coating Pan Operating Data
Charge = 1.9 Kg. plus color coating

| Elapsed Time (Min) | Solution Wt (g) Sprayed | Temperature, °F. Inlet | Temperature, °F. Outlet | PAN RPM | Pan Air Flow (CFM) | Atomizing Air (PSI) |
|---|---|---|---|---|---|---|
| 20 | 271 | 62.3 | 48.0 | 24.3 | 220 | 25.4 |
| 24 | 318 | 63.1 | 48.4 | 24.3 | 220 | 25.2 |
| 28 | 365 | 61.0 | 48.3 | 24.3 | 220 | 25.1 |
| 32 | 407 | 59.0 | 47.3 | 24.3 | 220 | 25.6 |
| 36 | 453 | 60.3 | 47.5 | 24.3 | 220 | 25.5 |
| 40 | 499 | 60.0 | 47.5 | 24.3 | 220 | 25.1 |
| 44 | 544 | 59.9 | 47.6 | 24.3 | 220 | 25.5 |
| 48 | 589 | 60.1 | 47.6 | 25.0 | 220 | 25.3 |
| 52 | 634 | 60.0 | 47.7 | 25.0 | 220 | 25.1 |
| 56 | 678 | 59.9 | 47.8 | 25.0 | 220 | 25.5 |
| 60:30 | 730 | 60.0 | 47.7 | 25.0 | 220 | 25.3 |
| 64:30 | 775 | 60.6 | 48.0 | 25.0 | 220 | 25.0 |
| 67:20 | 807 | 59.9 | 48.3 | 25.0 | 220 | 25.0 |

This application system employed one nozzle positioned 3" to 4" from the tablet bed and aimed at the bed of tablets to be coated. This produced an acceptable high gloss gellan gum coated placebo.

Samples were taken after weight gains of 0.05, 0.1, 0.2, 0.3, 0.4, 0.5, 0.6 and 0.7% respectively to document and monitor coating appearance and character.

This Example provided acceptable tablets with very high gloss and lubricious mouthfeel. This Example demonstrates the gloss and mouthfeel attributes of the gellan gum coating of this invention and also demonstrates the compatibility of clear gellan gum coating with a base coating of polymer and lake color system. Tablets of this Example had a gloss equal to or better than the gloss of commercially available sugar coated products.

EXAMPLE 2

In a first step, an acceptable gellan gum aqueous coating composition was prepared according to Example 1.

The tablets to be coated herein comprised uncoated placebos (⅜ inch, rounded shape, 355 mg. weigh each, standard concave shape). These uncoated placebos were first coated with a polymer/color composition comprising:

TABLE 4

| Ingredients: | Weight (g) |
|---|---|
| 606 (10%) | 2000 |
| SS-1092 | 125 |
| TA | 33 |
| Water | 200 |
| Total Weight | 2358 g |
| Brown (SS-1092) (40% solids): | |
| 37.2% Titanium Dioxide | 37.2 grams |
| 2.65% FD&C Yellow No. 6 Low dye Lake | 2.65 grams |
| 0.15% Red Iron Oxide | 0.15 grams |
| 2.0% EDTA solution (40%) | 2.00 grams |
| 58.0% Distilled Water | 58.00 grams |
| | 100.00 grams |
| SS = Spectrablends, from Warner-Jenkinson* | |

*Warner-Jenkinson: 107 Wade Avenue, South Plainfield, New Jersey 07080

This coating operation was carried out in a Compu Lab 15 inch side vented coating system in a manner similar to that employed for the color coating in Example 1, above.

These once coated placebos were then fed to a Compu Lab 15" pan side vented coating system wherein a gellan gum film coat ed high gloss tablet was prepared. One nozzle was employed which was positioned in close proximity to the bed of tablets to be coated.

Operating data is provided in Table 5 below.

TABLE 5

Side Vented Coating Pan Operating Data

| Elapsed Time (Min) | Solution Wt (g) Sprayed | Temperature, °F. Inlet | Temperature, °F. Outlet | PAN RPM | CFM | Atomizing Air PSI |
|---|---|---|---|---|---|---|
| 0 | 0 | 68.1 | 49.2 | 24.2 | 255 | 20.1 |
| 5:15 | 88 | 68.6 | 48.3 | 24.2 | 255 | 19.7 |
| 10:15 | 191 | 70.0 | 48.5 | 24.2 | 255 | 19.9 |
| 15 | 295 | 70.0 | 48.8 | 24.2 | 255 | 19.5 |
| 20:30 | 421 | 70.1 | 49.0 | 24.2 | 255 | 19.5 |
| 25 | 524 | 69.9 | 49.0 | 24.2 | 255 | 19.7 |
| 30 | 643 | 70.4 | 49.3 | 24.2 | 255 | 19.9 |
| 35 | 762 | 70.2 | 49.8 | 24.2 | 255 | 19.2 |

Samples were taken after weight gains of 0.1, 0.2, 0.3, 0.4, 0.5 and 0.6% respectively to monitor coating character. This Example provided acceptable tablets of this invention with high gloss and lubricious mouthfeel. This Example demonstrates the compatibility of clear gellan gum coating with polymer/oxide color systems in the base coat.

EXAMPLE 3

High gloss gellan gum film coated tablets were prepared by preparing in a first step a gellan gum composition as described in Example 1 above which contained 1.5% Kelcogel and 0.15% aspartame.

The tablets to be coated herein comprised uncoated placebos which were coated with a polymer/color composition comprising:

TABLE 6

| Ingredients: | Weight (g) |
|---|---|
| 606 (10%) | 600 |
| D452 (40%) | 24 |
| PEG460 | 12 |
| Water | 42 |
| Total Weight | 678 |
| Red (D452) (Dye Dispersion) | |
| 12.0% Titanium Dioxide | 420 grams |
| 20.0% FD&C Blue 1, Hi Dye Lake | 700 grams |
| 2.00% FD&C Yellow No. 6 dye | 70 grams |
| 6.0% FD&C Red No. 40 dye | 210 grams |
| 2.5% EDTA solution (40%) | 87.5 grams |
| 57.5% Distilled Water | 2012.5 grams |
| | 3500 grams |

The application was carried out in a Compu Lab side vented coating 15" pan, the data of which is shown in Step A below.

TABLE 7

Step A
Side Vented Coating Pan Operating Data

| Elapsed Time (Min) | Solution Wt (g) Sprayed | Temperature, °F. Inlet | Temperature, °F. Outlet | PAN RPM | CFM | Atomizing Air PSI |
|---|---|---|---|---|---|---|
| 0 | 0 | 69.9 | 47.4 | 15.0 | 245 | 42.1 |
| 6 | 95 | 70.2 | 45.5 | 15.0 | 250 | 41.4 |
| 8 | 137 | 70.2 | 46.6 | 15.0 | 250 | 41.3 |
| 12 | 213 | 69.9 | 46.9 | 14.9 | 250 | 41.4 |
| 17:10 | 305 | 67.3 | 46.5 | 15.0 | 235 | 39.9 |
| 18 | 323 | 67.6 | 46.3 | 14.9 | 235 | 39.7 |
| 20 | 362 | 68.0 | 46.6 | 14.8 | 235 | 39.6 |
| 24:10 | 493 | | | 15.1 | | |

The once color coated placebo from Step a above was then coated with a gellan gum aqueous composition in a Compu Lab side vented coating 15" pan in a Step B.

TABLE 8

Step B

| Elapsed Time (Min) | Solution Wt (g) Sprayed | Temperature, °F. Inlet | Temperature, °F. Outlet | PAN RPM | CFM | Atomizing Air PSI |
|---|---|---|---|---|---|---|
| 0 | 0 | 75.5 | 50.6 | 24.4 | 255 | 24.4 |
| 4 | 69 | 69.1 | 47.3 | 24.4 | 270 | 24.4 |
| 8 | 144 | 72.3 | 50.0 | 24.4 | 255 | 24.4 |
| 12 | 237 | 67.2 | 49.7 | 24.4 | 270 | 24.3 |
| 16 | 321 | 72.6 | 49.1 | 24.4 | 260 | 24.1 |
| 20 | 413 | 72.1 | 49.8 | 24.4 | 260 | 24.4 |
| 24:30 | 519 | 72.1 | 49.6 | 24.4 | 260 | 23.4 |
| 28:30 | 612 | 72.1 | 50.4 | 24.4 | 255 | 23.8 |

A sweet tasting high gloss acceptable coating was produced.

Samples were taken after weight gains of 0.1, 0.2, 0.3, 0.4 and 0.5% respectively to monitoring character. Acceptable tablets were prepared in this Example which had high gloss and lubricious mouthfeel. This demonstrates the compatibility of clear gellan gum coating with polymer/dye color systems in the base coat.

EXAMPLE 4

An acceptable tablet coating composition comprising a gellan gum composition was first prepared according to Example 1.

The tablets to be coated herein comprised uncoated active drug ingredient tablets of about 400 milligram (mg.) weight each, which were first coated with a polymer/color coating composition comprising:

TABLE 9

| Ingredients: | Weight (g) |
|---|---|
| Pharmacoat 606 (10%) | 100 |
| D-947 | 4 |
| TA | 2 |
| Water | 42 |
| Total Weight | 148 |

TABLE 9-continued

| Ingredients: | Weight (g) |
|---|---|
| Pink (D947) (Dye Dispersion) | |
| 37.6% Titanium Dioxide | 47 grams |
| 2.4% D&C Red No. 27 dye | 3 grams |
| 1.6% EDTA solution (40%) | 2 grams |
| 58.4% Distilled Water | 73 grams |
| | 125 grams |

TA = triacitin

A fluidized bed dryer system ("Wurster" type) was employed to carry out a first coating of these initially uncoated tablets. The fluidized bed system comprised a 4 inch circular plexiglass column having a perforated base plate with about 150 holes each about ⅛" diameter therein and having positioned in this base plate, a liquid spray nozzle which protruded about ¼ inch in the interior of the column above the base plate. The spray nozzle had a 0.035 inch diameter throat and was connected externally to a coating solution supply system. An air supply system was connected to the base plate and an air outlet filter positioned atop the column provided for the air outlet. The air supply system had a temperature regulator system on it. In operation the tablets to be coated were charged to this fluid bed dryer, compressed air was forced into and through the base plate and color coating composition was sprayed by the spray nozzle into the bed of tablets from the coating solution supply system.

TABLE 10

| Elapsed Time (Min) | Solution Wt(g) Sprayed | Feed | Outlet Temp ° F. | Blower | Compressor PSI |
|---|---|---|---|---|---|
| 0 | 11.3 | 2.2 | 120 | 5 | 32 |
| 4 | 65 | 2.2 | 120 | 5 | 36 |
| 8 | 20 | 2.2 | 116 | 5.5 | 36 |

An acceptable high gloss tablet was then prepared by coating over the color coated tablets prepared immediately above in the same fluidized bed dryer as described above by applying the previously made gellan gum coating composition of this Example to the color coated tablets. In this coated active product tablet, the color coat was the first coating (primary, initial, or base) and gellan gum was the second coating or overcoating.

TABLE 11

| Elapsed Time (Min) | Solution Wt(g) Sprayed | Feed | Outlet Temp ° F. | Blower | Compressor PSI |
|---|---|---|---|---|---|
| 0 | 0 | 2.5 | 120 | 5 | 32 |
| 4 | 46 | 2.5 | 120 | 5 | 32 |
| 8:10 | 92 | 2.5 | 122 | 5 | 32 |
| 12 | 134 | 2.6 | 122 | 5 | 32 |
| 16 | 179 | 2.6 | 122 | 5 | 32 |

Tablets produced in this Example were acceptable and had high gloss and lubricious mouthfeel. These tablets were essentially the same as the acceptable tablets produced in the previous Example. In this Example, a fluid bed system was employed as an application system whereas a side vented coating pan was employed as an application system in the previous Example.

EXAMPLE 5

An acceptable gellan gum coating composition was prepared according to Example 1.

The tablets to be coated herein comprised active ingredient tablets of about 476 mg weight each, which was first coated with a polymer/color coating composition comprising:

TABLE 12

| Ingredient | Weight |
|---|---|
| 606 (10%) | 100.0 |
| D-452 (40%) | 4.0 |
| PEG 400 | 2.0 |
| Water | 7.0 |
| Total Weight | 113.0 g |
| Red (D452) (Dye Dispersion) | |
| 12.0% Titanium Dioxide | 420 grams |
| 20.0% FD&C Blue 1, Hi Dye Lake | 700 grams |
| 2.00% FD&C Yellow No. 6 dye | 70 grams |
| 6.0% FD&C Red No. 40 dye | 210 grams |
| 2.5% EDTA solution (40%) | 87.5 grams |
| 57.5% Distilled Water | 2012.5 grams |
| | 3500 grams |

This first coating was carried out in a fluidized bed dryer as described in Example 4.

TABLE 13

| Elapsed Time (Min) | Solution Wt(g) Sprayed | Feed | Temperature, °F. Inlet | Outlet | Blower | Compressor PSI |
|---|---|---|---|---|---|---|
| 0 | 0 | 2.2 | 186 | 132 | 5 | 32 |
| 4 | 47 | 2.3 | 186 | 127 | 5 | 32 |
| 8 | 87 | 2.3 | 186 | 127 | 5 | 32 |
| 10:30 | 108 | 2.3 | 187 | 129 | 5 | 32 |

In a second step of this Example 5, a high gloss gellan gum film coated tablet was prepared by coating the once coated tablet prepared immediately above in a fluidized bed dryer as described above with a gellan gum composition, the data of which follows in Table 14.

TABLE 14

| Elapsed Time (Min) | Solution Wt(g) Sprayed | Feed | Temperature, °F. Inlet | Outlet | Blower | Compressor PSI |
|---|---|---|---|---|---|---|
| 5 | 53 | 2.35 | 179 | 127 | 5 | 32 |
| 9 | 89 | 2.4 | 179 | 128 | 5 | 32 |
| 14 | 137 | 2.4 | 178 | 127 | 5 | 32 |
| 21:30 | 200 | 2.4 | 176 | 125 | 5 | 32 |

Tablets produced in this Example were acceptable and had a high gloss film coat and lubricious mouthfeel. These tablets were essentially the same as the acceptable tablets produced in the previous Example.

EXAMPLE 6

Application of a Clear Gellan Gum Film Coating to an Uncoated Tablet

Purpose: To apply clear coating of an aqueous gellan gum composition to uncoated uncolored tablets to provide an acceptable high gloss coated tablet of this invention.

Method: Using a 1.5% gellan gum solution useful for coating tablets

| % | Grams |
|---|---|
| 1.5% Gellan Gum | 22.5 grams |
| 0.10% Sodium Citrate** | 1.5 grams |
| 98.4% Deionized Water | 1476.0 grams |
| | 1500 grams |

**Dihydrate, powder

Using a suitable mixing blade and mixer, with good vortex the gellan gum was slowly added to water. Once the gellan gum was dispersed sodium citrate was added and heating initiated. Heat to 70° C. Allow solution to cool and form gel.

Coating procedure: Spray 200 grams of 1.5% gellan solution (room temperature) onto 420 grams uncolored active ingredient tablets using a laboratory fluidized column (similar in concept to an Aeromatic Strea 1). Samples of tablets were taken at 0.05, 0.1, 0.2, 0.3, 0.4 and 0.5% weight gains respectfully.

Application of 1.5% Gellan Gum to Uncoated Tablet

| Time Min. | Weight Sprayed Grams | Inlet Temp (° F.) | Exhaust Temp (° F.) | Pump Setting | Compressor PSI |
|---|---|---|---|---|---|
| 0 | 5.5 | 162 | 127 | 2.5 | 32 |
| 4:30 | 58.5 | 168 | 119 | 2.5 | 30 |
| 8:30 | 100.0 | 173 | 123 | 2.5 | 32 |
| 13:00 | 146.5 | 173 | 123 | 2.5 | 32 |
| 16:00 | 177.5 | 175 | 123 | 2.5 | 32 |
| 18:40 | 200 | 175 | 123 | 2.5 | 32 |

In this Example, acceptable tablets were produced which had very high gloss and lubricious mouthfeel. This Example demonstrates that gellan gum film coating of this invention can be successfully coated onto a tablet absent a base coating on that tablet. The resulting gloss was judged superior to commercially available clear coatings (non gellan gum) and commercially available sugar coatings.

EXAMPLE 7

Preparation and evaluation of the viscosity of 1.8% and 2.0% gellan gum composition to be measured for viscosity over a temperature range of about room temperature to about 60° C. and also to be coated onto color coated tablets.

These solutions of gellan gum were sprayed onto color coated tablets at temperatures between 24° C. and 30° C. (with viscosities ranging from +28,000 cps to 55,000 cps).

Materials: Gellan Gum
    Deionized Water
    Na Citrate Procedure: a 1.8% gellan and a 2% gellan solution were made as Example 1

| | 1.8% | | |
|---|---|---|---|
| Gellan Gum | = | 1.8% | = | 27.9 g |
| Deionized Water | = | 98.08% | = | 1471.2 g |

-continued

| | | | | |
|---|---|---|---|---|
| Na Citrate | = | 0.12% | = | 1.8 g |
| | | 2.0% | TOTAL | 1500 g |
| Gellan Gum | = | 2.0% | = | 30.0 g |
| Deionized Water | = | 97.87% | = | 1468.05 g |
| Na Citrate | = | 0.13% | = | 1.95 g |
| | | | TOTAL | 1500 g |

Viscosity Measurements:
  Spindle=3, Vessel=600 ml beaker, DV-I+ Brookfield Viscometer, Viscosity was while solutions cooled.

| 1.8% by wt. Gellan Gum | | | 2.0% by wt. Gellan Gum | | |
|---|---|---|---|---|---|
| Temp. °C. | Viscosity (cp) | Speed RPM | Temp °C. | Viscosity (cp) | Speed RPM |
| — | — | — | — | — | — |
| 60 | 44 | 100 | — | — | — |
| 50 | 60 | 100 | 48 | 89 | 100 |
| 40 | 127 | 100 | 40 | 164 | 100 |
| 35 | 2200 | 50 | 34.6 | 17680 | 5 |
| *30 | 28460 | 2.5 | 30 | 39740 | 2.5 |
| **25 | 38730 | 2.5 | *28 | 45600 | 2.0 |
| — | — | — | **24.6 | 55440 | 2.0 |

Key:
*Viscosity measured before start of coating application to tablets
**Viscosity measured after coating application was completed to tablets
1.8% Gellan gum Brookfield Engineering Laboratories, Inc.,240 Cushing Street, Stoughton, Mass. 02072-2398

Application as a Coating to a Tablet Using a Fluid Bed Dryer

| Time Min. | Weight Sprayed | Inlet Temp °F. | Exhaust Temp °F. | Pump Setting | Compressor PSI | H/B |
|---|---|---|---|---|---|---|
| 0 | 5.5 | 158 | 131 | 2.5 | 32 | H8 |
| 4:00 | 54.0 | 103 | 121 | 2.5 | 30 | B5 |
| 8:00 | 92.0 | 167 | 122 | 2.5 | 32 | B5 |
| 12:30 | 137.5 | 168 | 122 | 2.5 | 31 | B5 |
| 16:30 | 176.5 | 167 | 123 | 2.5 | 32 | B5 |
| 20:00 | 200 | 169 | 123 | 2.5 | 32 | B5 |

The temperature of 1.8% Gellan at end of run was 26.0° C.
2% Gellan Gum

Application as a Coating to a Tablet Using a Fluid Bed Dryer

| Time Min. | Weight Sprayed | Inlet Temp °F. | Exhaust Temp °F. | Pump Setting | Compressor PSI | H/B |
|---|---|---|---|---|---|---|
| 0 | 6.0 | 174 | 140 | 3.0 | 32 | H8 |
| 1:00 | 22.0 | 170 | 128 | 3.0 | 32 | |
| 4:00 | 72.0 | 174 | 119 | 2.5 | 32 | |
| 8:00 | 113.0 | 177 | 127 | 2.5 | 32 | H8 |
| 14:00 | 180.0 | 176 | 127 | 2.5 | 32 | B5.6 |
| 15:45 | 200 | 178 | 128 | 2.5 | 32 | |

There was no problem spraying an aqueous gellan gum composition at 1.8% or 2.0% at room temperature at a viscosity ranges between about 28,460 cps at about 55,500 cps using conventional peristaltic pumping and standard nozzle apparatus.

Samples were taken after weight gains of 0.05, 0.1, 0.2, 0.3, 0.4 and 0.5% respectively to monitor coating character. In this Example, acceptable tablets were produced having high gloss and lubricious mouthfeel. This Example showed that gellan gum aqueous coating compositions can be successfully employed according to this invention at 1.5%, 1.8% and 2.0% solids. Gloss and mouthfeel are not compromised when applying (via spraying) higher solids coating compositions.

EXAMPLE 8

Preparation of a 1.8% by weight and 2.0% by weight aqueous gellan solution to be used for spraying a clear coating of gellan gum onto a color coated tablet. The gellan gum solutions will be sprayed at an elevated temperature.
  Materials: Gellan Gum
    Deionized Water
    Na Citrate
  Procedure: Solutions were made:

| 1.8% Gellan Solution (1L) Prepared | | | | |
|---|---|---|---|---|
| Gellan Gum | = | 1.8% | = | 18.0 g |
| Deionized Water | = | 98.08% | = | 980.8 g |
| Na Citrate | = | 0.12% | = | 1.2 g |
| | | | TOTAL | 1000 g |
| 2.0% Gellan Solution (2L) Prepared | | | | |
| Gellan Gum | = | 2.0% | = | 40 g |
| Deionized Water | = | 97.87% | = | 1957.4 g |
| Na Citrate | = | 0.13% | = | 2.6 g |
| | | | TOTAL | 2000 g |

Prepared gellan solutions (1.8% concentration and 2.0% concentration) were then sprayed onto tablets using the fluid bed coating equipment. The solution were sprayed at 40° C. where viscosity of each solution is below 200 cps.
  1.8% Gellan Gum Solution at 40° C.

| Time | Weight Sprayed | Inlet Temp °F. | Exhaust Temp °F. | Pump Setting | Compressor PSI |
|---|---|---|---|---|---|
| 0 | 0 | 142 | 125 | 2.3 | 32 |
| 4:00 | 32 | 159 | 127 | 2.3 | 32 |
| 8:30 | 75.5 | 172 | 125 | 2.3 | 32 |
| 12:00 | 109.5 | 169 | 126 | 2.3 | 32 |
| 18:25 | 166.6 | 164 | 125 | 2.3 | 32 |

2.0% Gellan Gum Solution at 40° C.

| Time | Weight Sprayed | Inlet Temp °F. | Exhaust Temp °F. | Pump Setting | Compressor PSI |
|---|---|---|---|---|---|
| 0 | 0 | 150 | 127 | 2.3 | 32 |
| 8:00 | 75.5 | 168 | 127 | 2.3 | 32 |
| 14:00 | 174.5 | 166 | 127 | 2.3 | 32 |
| 16:42 | 150 | 165 | 128 | 2.3 | 32 |

Heating the solution to lower viscosity had no detrimental effect on the coating delivered to the tablets. Spraying at elevated temperatures allows for high solids at lower viscosity and delivers a film comparable to lower solid solutions sprayed at room temperature.

EXAMPLE 9

Gellan with pigment sprayed onto tablets. Pigment addition to gellan coating solutions at room temperature is difficult due to viscosity of gellan solution. Pigment is easily dispersed, however, when gellan coating solution is heated to 40° C. or above. At this temperature the coating solution is fluid (viscosity below 200 cps) and dispersion of pigments in gellan solution is easily achieved with a standard laboratory mixer. Gellan solution: Follow procedure recited in Example 1.

| Formula: | |
|---|---|
| 1.5% Gellan gum | 45 grams |
| 0.1% Sodium Citrate | 3 grams |
| 98.4% Deionized Water | 2952 grams |

Sodium Citrate (a sequestrant)

1000 grams of above gellan coating solution (1.5% gellan) is held at 40° C. To this preparation is added 3.0 grams Propylene Glycol and 3.0 grams of Lecithin (Alcolec F-100) while mixing. The color component (7.5 grams of Green—Spectra Spray SS-1091) is added but while mixing and holding solution temperature at 40° C. or above. Mix until homogenous.

Grams of gellan/color preparation from above was then sprayed onto 420 grams of tablets in a fluidized bed coating apparatus. The 420 grams of tablets is a combination of 25 grams of tablets with active ingredients and 395 grams of placebo tablets. Samples of tablets were taken at 0.5, 1.0, 2.0, 2.5 and 3.0% weight gains respectively.

Tablets prepared in this Example had high gloss, uniform color and lubricious mouthfeel. This Example demonstrates the compatibility of gellan gum with lake color system for aqueous film coating.

EXAMPLE 10

Gellan Clear Coating Sprayed on Gellan/color Coated Tablets From Example 9

Tablets from Example 9 which were coated with gellan and color coating solution (gellan, Green Spectra Spray, Propylene Glycol and Lecithin) were taken and coated again with a clear gellan coating solution also sprayed at 40° C. (1.5% gellan). This demonstrates the compatibility of gellan/color coating with gellan when used as a top coating or gloss coat. The top coating of clear gellan was applied at 40° C. with a total weight gain of 0.5%. Samples were taken at 0.05%, 0.1%, 0.2%, 0.3%, 0.4% and 0.5% with gloss increasing with each additional weight gain of clear coating.

Tablets prepared in this Example had a higher gloss than the tablets of Example 9. These tablets also had a lubricious mouthfeel. This Example demonstrates the ability of this invention to improve tablet gloss when using clear gellan gum coating as an overcoat or as a gloss coating. This Example also demonstrates the compatibility of gellan gum coating with a base coat comprising gellan gum and lake color. Coated tablets produced herein have gloss and appearance which is better than or equivalent to commercially manufactured sugar coated tablets.

EXAMPLE 11

Gellan Gum with Pigment (Oxides)

Using 1.5% gellan gum solution prepared in example 11, maintain gellan solution at 40" C. and add color/plasticizer system as in example 10.

Color system added to 1000 gram gellan solution:

3.0 grams Lecithin (Alcolec F-100)

3.0 grams propylene glycol 7.5 grams Oxide (Spectra Spray 1092)

Pigment disperses easily in gellan solution at 40° C. because of low viscosity of heated solution.

760.1 grams of gellan/oxide preparation were sprayed at 40° C. onto 420 grams of tablets in a fluidized columns (similar to Aeromatic Strea 1). Samples were taken at 0.05%, 0.1%, 0.2%, 0.3%, 0.4% and 0.5% weight gains.

Tablets were produced in this Example that had high gloss, uniform color and lubricious mouthfeel. This Example demonstrates the compatibility of gellan gum with lake color systems and plasticizer in aqueous film coating systems.

EXAMPLE 12

Gellan Gum Coating on Vitamin Tablets and Placebos

Purpose: To apply clear coating of Gellan gum solution to colored vitamin tablets to demonstrate that appropriate gloss can be obtained.

Method: Using a 1.5% Gellan solution:

1500 grams total:

| % | Grams |
|---|---|
| 1.5% Gellan Gum (Ex 8096*) | 22.5 grams |
| 0.10% Sodium Citrate** | 1.5 grams |
| 98.4% Deionized Water | 1476 grams |

**Dihydrate, powder

Mixing Instructions: Follow procedure recited in Example 1.

Coating Instructions: Follow procedure recited in Example 4 (sprayed at room temperature).

Tablets used totaled 420 grams (210 grams peach colored vitamins and 210 grams of uncoated placebo tablets).

In this Example, acceptable coated tablets were also produced which result in vitamin tablets and placebo tablets that had high gloss and lubricious mouthfeel. This Example demonstrates that gellan gum applied as a clear aqueous coating in accordance with this invention is compatable with vitamins and placebo tablets and results in tablets having an improved gloss and mouthfeel over uncoated tablets.

EXAMPLE 13

Gellan Gum Coating on Vitamin Tablets and Placebos Sprayed at 40° C.

Purpose: To apply clear coating of Gellan gum solution to colored vitamin tablets to determine if appropriate gloss can be obtained.

Method: Using a 1.5% Gellan solution:

1500 grams total:

| % | Grams |
|---|---|
| 1.5% Gellan Gum (Ex 8096*) | 22.5 grams |
| 0.10% Sodium Citrate** | 1.5 grams |
| 98.4% Deionized Water | 1470.0 grams |

**Dihydrate, powder

Mixing Instructions: Follow procedure recited in Example 1.

Coating Instructions: Follow procedure recited in Example 1 (sprayed at 40° C.).

Tablets used totaled 420 grams (210 grams peach colored vitamins and 210 grams of uncoated placebo tablets).

In this Example, acceptable coated tablets were produced in accordance with this invention which had high gloss and lubricious mouthfeel comparable to the tablets from Example 13. This Example demonstrates that ability of gellan gum to be processed in accordance with this invention at elevated temperatures with no negative impact on gloss or mouthfeel of the coated tablets.

EXAMPLE 14

Gellan Gum with Pigment: Lake with PEG 400 Increased*
*Rather than 20% PEG 400 of total gellan gum solids, 50% PEG 400 of gellan solids will be evaluated.

Gellan solution preparation: Follow procedure recited in Example 1.

Mixing instructions: Follow procedure recited in Example 1.

Coating Preparation:
600 grams 1.5% Gellan solution (heated to 40° C.)
4.5 grams Peach (SS-094)
4.5 grams PEG 400
   Peach (SS-1 094) (40% solids)
   37.2% titanium dioxide 37.2 grams
   2.65% FD&C yellow no. 6 low dye lake
   0.15% red iron oxide 0.15 grams
   2.0% EDTA solution (40%) 2.00 grams
   58.0% distilled water 58.00 grams Coating trial: (5-71-74-2) Spray 581.5 grams of above formula (40° C.) onto 420 grams placebos using a fluidized column (similar in concept to an Aeromatic Strea 1). Samples of tablets taken at 0.5, 1.0, 1.5, 2.05 weight gains.

This resulted in improved and acceptable film flexibility, improved gloss and good tablet coverage. This Example results in acceptable tablets with high gloss and lubricious mouthfeel. This Example demonstrates the compatibility of gellan gum with lake color systems and plasticizer at elevated concentrations. The elevated plasticizer level enables greater film flexibility.

EXAMPLE 15

Gellan Gum with Pigment: White Formula
*Gellan solution preparation: Used 1000 grams from solution made above, which had cooled to around 40° C.

Coating preparation:
1000 grams 1.5% gellan solution
9.4 grams White (SS-1031) (50% solids).
3.0 grams Propylene. Glycol
3.0 grams Lecithin (Alcolec F-100)
   White (SS-1031) (50%) solids
   25% titanium dioxide 50 grams
   25% talc 50 grams
   2.5% EDTA solution (40%) 5 grams
   47.5% distilled water 95 grams Weigh gellan solution into appropriate beaker (37.5° C.). Add Propylene Glycol and lecithin. Stir, with an appropriate stirrer until it is mixed well. Add white dispersion. Keep temperature around 40° C. prior to spraying. Combined at this temperature, pigment dispersed easily and mixed into the gellan solution with no problems.

Coating trial: Spray 711.2 grams of above formula (40° C.) 420 grams placebos* using a fluidized column (similar in concept to Aeromatic Strea 1). Samples of tablets taken at 0.5, 1.0, 1.5, 2.0, 2.5, 3.0% weight gains.
*25 grams active tablets part of charge The Example produced acceptable tablets that had good lubricious mouthfeel and gloss characteristics that are higher than commercially available white coating systems. This example demonstrates that gellan gum is compatible with titanium based color systems and plasticizers. This example also demonstrates gellan gum's ability to impart :gloss in the presence of these ingredients.

EXAMPLE 16

Gellan gum with pigment: lake (with HPMC addition) Using 1.5% gellan solution prepared above.

Coating preparation:
1000 grams 1.5% gellan solution
7.5 grams Green (SS-1091)
3.0 grams Hydroxypropylmethylcellulose (pharmacoat 606)
3.0 grams PEG 400
where PEG=polyethylene glycol 400 and Green (SS-1091) comprised:

| | |
|---|---|
| 38.4% titanium dioxide | 76.8 grams |
| 2.65% FD&C yellow No. 6 low dye lake | 2.65 grams |
| 0.15% red iron oxide | 0.15 grams |
| 2.0% EDTA solution (40%) | 2.00 grams |

58.0% distilled water 58.00 grams for a total f 200 grams

Weigh gellan solution into appropriate beaker and heat. Add PEG 400 and HPMC (temperature when added=60° C.). Mix with an appropriate stirrer until dissolved. Add lake dispersion until it is mixed well.

Coating trial: Spray 760.1 grams of above formula (40° C.) 420 grams placebos* using a fluidized column (similar in concept to an Aeromatic Strea 1). Samples of tablets taken at 0.5, 1.0, 1.5, 2.0, 2.5, 3.0% weight gains.
*25 grams active tablets as part of charge (charge is the tablets to be coated which are provided to the fluidized column)

Results: Tablets coated to a 3% weight gain; addition of HPMC improved film flexibility and enabled formulae to be made with PEG added at a standard level (20% of gellan solids level); gloss was not compromised and is close to that which was obtained in tests using gellan with lecithin and PG. This Example further resulted in acceptable tablets with a higher gloss than tablets coated with HPMC alone. Also, the tablets of this Example prepared in accordance with this invention, had the lubricious mouthfeel characteristic of gellan gum coatings. Further, this Example demonstrated the compatibility of gellan gum with HPMC.

EXAMPLE 17

Use of a side vented coating pan as a successful application system
A:
24" pan Accela Cotta 16 Kg. charge color coated
1.5% gellan gum, pan RPM 13
Process air Vol. 440CFM
T=72° C. (Inlet)
Exhaust air temperature 50–52° C.

Two ¼ Jau Tips 40100 liq cap. (0.040 inch internal diameters, 0.100 inch external diameter from Spray Systems)

134255-45 Air cap.

Atomizing Pressure 24–25 PSI

Feed Rate 55–70g/min

B:

60" Pan Acella Coata successful coating Charge 350 KG

| Process | Color Coat | Gellan Gum Coat |
|---|---|---|
| Air Volume | 5500 cfm | 5500 cfm |
| Temperature | 70° F. | 75° F. (Inlet) |
| Exhaust T | 47 | 52 |
| Spray Rate | 1200 g/m | 1200 g/min |
| Solids | 12% | 1.5% |
| Atomizing Air | 40 psi | 25 psi |

The Example provided acceptable tablets with high gloss and lubricious mouthfeel. This Example demonstrates the ability of gellan gum aqueous film coating system of this invention to be operated and scaled up from bench top equipment to a commercial size equipment.

EXAMPLE 18

Gellan Gum Coating Solution with Dye Dispersion

A tablet coating composition comprised of a gellan gum composition was first prepared (1.5% gellan concentration) according to Example 1. Tablets (420 grams) were coated using a fluidized column (similar in concept to an Aeromatic Strea 1). These tablets were coated with a polymer/color coating composition and the gel gum solution which were combined as follows:

1000 grams 1.5% gellan solution 3.75 grams Green dye dispersion (D412)

3.0 grams Propylene Glycol 3.0 grams Lecithin (Alcolec F-100)

Weigh the gellan into a beaker and add the propylene glycol and lecithin while gellan preparation in +40° C. Once the propylene glycol and lecithin are dispersed, add the dye dispersion.

807.8 grams of above formula were sprayed onto 420 grams of tablets (395 grams of placebos and 25 grams of tablets with active drug substance).

| Run | Time | Weight | Inlet Temp ° F. | Exhaust Temp ° F. | Pump Setting | Comp Setting | Heater/Blower H | Heater/Blower B |
|---|---|---|---|---|---|---|---|---|
| 57184-1 | 0 | 5.5 | 175 | 123 | 2.2 | 32 | | |
| | 8:00 | 89.5 | 187 | 126 | 2.3 | 32 | 9 | 5.3 |
| | 15:00 | 181.5 | 190 | 124 | 2.5 | 32 | | |
| | 23:00 | 287.0 | 190 | 123 | 2.5 | 32 | | |
| | 30:00 | 381.5 | 190 | 123 | 2.5 | 32 | | |
| | 35:00 | 450.0 | 191 | 123 | 2.5 | 32 | | |
| | 45:00 | 593.0 | 191 | 124 | 2.5 | 32 | | |
| | 60:00 | 787.5 | 191 | 125 | 2.5 | 32 | | |
| | 61:45 | 812.5 | 192 | 126 | 2.5 | 32 | | |

This Example provided acceptable tablets with very high gloss and lubricious mouthfeel. This Example further demonstrates the compatibility of gellan gum with dye color systems and plasticizer.

EXAMPLE 19

Four tablets were compared:

| A | MOTRIN tablet with manufacture coating |
|---|---|
| B | MOTRIN tablet with manufacture coating plus 0.3% weight gain of coating containing 1.5% Gellan Gum |
| C | MOTRIN tablet with manufacture coating plus 0.3% weight gain of coating containing 1.5% Gellan Gum & 0.15% PEG 400 plasticizer |
| D | MOTRIN tablet with manufacture coating plus 0.3% weight gain of coating containing 1.5% Gellan Gum, 0.15% PEG 400 plasticizer & 0.45% EPIKURON 100 |

Figure 1:
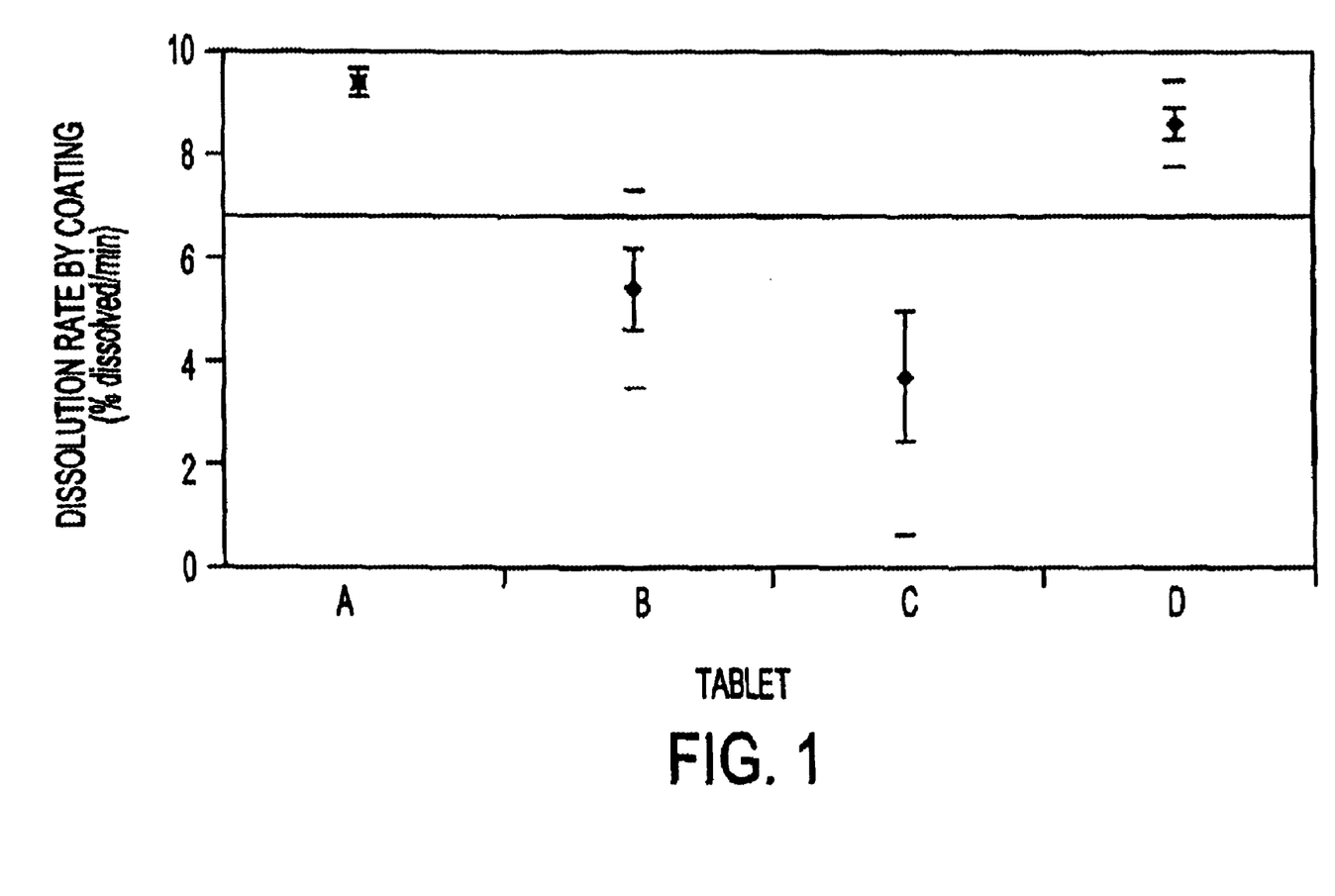
FIG. 1 depicts the dissolution rate of tablets with different coating compositions.

Attention is drawn to FIG. 1 which shows the dissolution rate (% dissolved/minute) of the four tablets. Tablets A and D had virtually the same dissolution rate. Tablet B had slower dissolution than uncoated tablets because gellan gum alone was coated onto the tablets without a disintegration aid. Tablet C had the slowest dissolution rate because gellan gum and plasticizer coated on the tablet, formed an almost impermeable elastic film that prevents drug release. This example shows that a composition containing gellan gum, plasticizer, and lecithin provides adequate dissolution and effective drug delivery system.

EXAMPLE 20

An aqueous gellan gum solution was prepared with the following ingredients and coated on a placebo:

| 95.12 wt % water | 10463.2 g |
|---|---|
| 2.5 wt % gellan gum | 275 g |
| 0.17 wt % NaCitrate | 18.7 g |
| 0.17 wt % MPB | 18.7 g |
| 1.0 wt % propylene glycol | 110 g |
| 1.25 wt % TiO2 (60%) | 137.5 g |
| 0.3 wt % ethyl vanillin | 33 g |
| 0.25% EPIKURON (lecithin) | 27.5 g |
| 0.08 wt % caramel color | 8.8 g |
| Total | 11000.0 g |

The resulting aqueous composition had 4.88 wt % solids. The composition was coated on a placebo using a 24" pan and a 0.040" spray system, ⅛ VAU two gun spray system.

A clear coat was coated over the above coating.

| 95.91 wt % water | 2877.3 g |
|---|---|
| 2.5 wt % gellan gum | 75 g |
| 0.25 wt % EPIKURON | 7.5 g |
| 0.17 wt % NaCitrate | 5.1 g |
| 0.17 wt % MPB | 5.1 g |
| 1.0 wt % propylene glycol | 30 g |
| Total | 3000 g |

The coated tablets show the compatibility of the pigmented gellan coating system with a flavor, ethyl vanillin, and feasibility of a gellan clear coat over a gellan system pigmented and containing flavor.

EXAMPLE 21

An aqueous gellan gum solution was prepared with the following ingredients:

| | | |
|---|---|---|
| 97.17 wt % water | 971.7 g |
| 1.5 wt % gellan gum | 15 g |
| 0.1 wt % NaCitrate | 1 g |
| 0.1 wt % MPB | 1 g |
| 0.75 wt % EPIKURON | 2.5 g |
| 0.5 wt % Pure Coat (Starch) | 5 g |
| 0.3 wt % propylene glycol | 3 g |
| 0.04 wt % Aspartame | 0.4 g |
| 0.04 wt % Sweet AM | 0.4 g |
| Total | 1000 g |

The resulting clear aqueous composition had 2.83 wt % solids. The composition was coated on a placebo using a 15" pan and a 0.040" ¼ JAU single gun spray system.

Coating and disintegration tests showed the compatibility of the gellan coating system with sweeteners.

EXAMPLE 22

An aqueous gellan gum solution was prepared with the following ingredients and coated on a placebo:

| | | |
|---|---|---|
| 95.33 wt % water | 333 g |
| 2.5 wt % gellan gum | 87.5 g |
| 0.75 wt % Pure Coat | 26.25 g |
| 0.17 wt % NaCitrate | 5.95 g |
| 1.0 wt % propylene glycol | 3.5 g |
| 0.25% EPIKURON | 8.75 g |
| Total | 3500 g |

The composition was coated on a lacebo using a 24" pan and a 0.040" ¼ JAU two gun spray system.

The coated tablets shows the compatibility of Gellan at 2.5 wt % concentration with the other coating constituents, i.e. lecithin, starch, and plasticizers.

EXAMPLE 23

An aqueous gellan gum solution was prepared with the following ingredients and coated on a placebo:

| | | |
|---|---|---|
| 96.87 wt % water | 968.7 g |
| 2.0 wt % gellan gum | 20 g |
| 0.13 wt % NaCitrate | 1.3 g |
| 0.8 wt % propylene glycol | 8 g |
| 0.2% EPIKURON | 2 g |
| Total | 1000 g |

The composition was coated on a placebo using a 15" pan and a 0.040"¼ JAU single gun 60° Air Cap spray system.

The coated tablets demonstrate the feasibility of gellan gum at 2.0% concentration with other coating system constituents, i.e. starch, plasticizer, lecithin (EPIKURON) and the compatibility of gellan gum with the 60° Air Cap spray system.

EXAMPLE 24

An aqueous gellan gum solution was prepared with the following ingredients and coated on a placebo:

| | | |
|---|---|---|
| 97.1 wt % water | 485.5 g |
| 1.5 wt % gellan gum | 7.5 g |
| 0.5 wt % Pure Coat | 2.5 g |
| 0.1 wt % NaCitrate | 0.5 g |
| 0.6 wt % propylene glycol | 3 g |
| 0.2 wt % EPIKURON | 1 g |
| Total | 500 g |

The composition was coated on a placebo using a 15" pan and a 0.040" ¼ JAU single gun spray system.

The coated tablets demonstrate the compatibility of gellan gum at 1.5 wt % concentration with other coating system constituents, i.e. starch, plasticizer, lecithin (EPIKURON).

EXAMPLE 25

An aqueous gellan gum solution was prepared with the following ingredients and coated on a placebo:

95.16 wt % water 2.5 wt % gellan gum 0.75 wt % Pure Coat 0.25 wt % EPIKURON 0.1 7 wt % NaCitrate 0.17 wt % MPB 1.0 wt % propylene glycol The composition was coated on a placebo using a 48" pan and ⅛ VAU four gun spray system.

The coated tablets demonstrate the compatibility/feasibility of gellan gum at 2.5 wt % concentration in 48" pan.

EXAMPLE 26

An aqueous gellan gum solution was prepared with the following ingredients and coated on a placebo:

96.24 wt % water 2.0 wt % gellan gum 0.2 wt % EPIKURON 0.13 wt % NaCitrate 0.13 wt % MPB 0.8 wt % propylene glycol 0.5 wt % Pure Coat The composition was coated on a placebo using a 48 " pan and ⅛ VAU four gun spray system.

The coated tablets demonstrate the compatibility/feasibility of gellan gum at 2.0 wt % concentration with starch, plasticizer, and lecithin in 48" pan.

EXAMPLE 27

An aqueous gellan gum solution was prepared with the following ingredients and coated on a placebo:

96.74 wt % water 2.0 wt % gellan gum 0.2 wt % EPIKURON 0.13 wt % NaCitrate 0.13wt % MPB 0.8 wt % propylene glycol The composition was coated on a placebo using a 48 " pan.

The coated tablets demonstrate the compatibility/feasibility of gellan gum at 2.0 wt % concentration in 48" pan with lecithin and plasticizer.

Thus, it is apparent that there has been provided, in accordance with the instant invention, a process that fully satisfies the objects and advantages set forth herein above. While the invention has been described with respect to various specific examples and embodiments thereof, it is understood that the invention is not limited thereto and many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A film coated tablet comprising a tablet film coated with a gellan gum coating consisting essentially of gellan gum and effective amounts of a plasticizer and a disintegration aid, and optionally an effective amount of a slip enhancer.

2. The film coated tablet of claim 1 wherein the gellan gum coating comprises from about 0.025 wt % to about 10 wt % of the total tablet weight.

3. The film coated tablet of claim 2 wherein the gellan gum coating comprises from about 0.05 wt % to about 5 wt % of the total tablet weight.

4. The film coated tablet of claim 3 wherein the gellen gum coating comprises from about 0.075 wt % to about 3 wt % of the total tablet weight.

5. The film coated tablet of claim 1 wherein the plasticizer is selected from the group consisting of propylene glycol, polyethylene glycol 400, polyethylene glycol 3350, polyethylene glycol 8000, glycerol triacetate, polysorbate 80, triethyl citrate, PLAS 2, and acetylated monoglycerides.

6. The film coated tablet of claim 1 wherein the disintegration aid is selected from the group consisting of lecithin, pregelatinized modified corn starch, glyceryl carpylate, sorbitan oleate, and sodium lauryl sulfate.

7. The film coated tablet of claim 1 wherein the gellan gum coating is at least one of a primary coating, a secondary coating, or a tertiary coating.

8. The film coated tablet of claim 1 wherein the gellan gum coating is the only coating.

9. The film coated tablet of claim 1 wherein the gellan gum coating further includes a color.

10. A film coated tablet comprising a primary coating and a secondary coating, wherein one of the primary coating or secondary coating consists essentially of gellan gum and effective amounts of a plasticizer and a disintegration aid, and optionally, an effective amount of a slip enhancer.

11. The film coated tablet of claim 10 wherein the other of the primary coating or secondary coating comprises a polymer other than gellan gum.

12. The film coated tablet of claim 10 wherein the primary coating consists essentially of gellan gum and effective amounts of a plasticizer and a disintegration aid, and optionally, an effective amount of a slip enhancer and a color and the secondary coating comprises gellan gum.

13. The film coated tablet of claim 1 having a level of gloss of about 200 to about 400 when characterization is done using a surface system analyzer.

14. The film coated tablet of claim 13 wherein the level of gloss is from about 250 to about 350.

15. The film coated tablet of claim 1 wherein the tablet comprises an active drug.

16. A film coated tablet comprising a tablet coated with a gellan gum coating made by the process comprising forming the gellan gum coating by spraying onto the tablet an aqueous solution consisting essentially of gellan gum and effective amounts of a plasticizer and a disintegration aid, and optionally an effective amount of a slip enhancer.

17. The film coated tablet of claim 16 wherein the aqueous solution contains about 0.1 wt % to about 10 wt % by weight gellan gum based on total weight of the aqueous solution.

18. The film coated tablet of claim 17 wherein the aqueous solution contains about 0.5 wt % to about 5 wt % gellan gum based on total weight of the aqueous solution.

19. The film coated tablet of claim 18 wherein the aqueous solution contains about 0.5 wt % to about 3.5 wt % gellan gum based on total weight of the aqueous solution.

20. The film coated tablet of claim 16 wherein the aqueous solution contains about 0.01 wt % to about 10 wt % of the plasticizer based on total weight of the aqueous composition.

21. The film coated tablet of claim 16 wherein the aqueous solution contains about 0.01 wt % to about 10 wt % of the disintegration aid based on total weight of the aqueous composition.

* * * * *